US012699453B2

(12) United States Patent
Lee et al.

(10) Patent No.: US 12,699,453 B2
(45) Date of Patent: Aug. 4, 2026

(54) BIO-SIGNAL DETECTION APPARATUS, OPERATING METHOD OF BIO-SIGNAL DETECTION APPARATUS, AND USER TERMINAL COMPRISING BIO-SIGNAL DETECTION APPARATUS CAPABLE OF LEARNING ARRANGEMENT OF BIO-SIGNAL SENSING ELECTRODES

(71) Applicant: SAMSUNG ELECTRONICS CO., LTD., Suwon-si (KR)

(72) Inventors: Dongseop Lee, Suwon-si (KR); Jiwon Hyung, Suwon-si (KR); Hakjung Kim, Suwon-si (KR); Daniel Dongyuel Lee, Suwon-si (KR); Yusun Son, Suwon-si (KR); Dojun Yang, Suwon-si (KR); Keunseok Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 19/025,027

(22) Filed: Jan. 16, 2025

(65) Prior Publication Data

US 2025/0155978 A1 May 15, 2025

Related U.S. Application Data

(63) Continuation of application No. PCT/KR2023/010295, filed on Jul. 18, 2023.

(30) Foreign Application Priority Data

| Sep. 7, 2022 | (KR) | .......................... | 10-2022-0113796 |
| Nov. 2, 2022 | (KR) | .......................... | 10-2022-0144621 |

(51) Int. Cl.
| *G06F 3/01* | (2006.01) |
| *A61B 5/00* | (2006.01) |
| *A61B 5/276* | (2021.01) |

(52) U.S. Cl.
CPC .............. *G06F 3/015* (2013.01); *A61B 5/276* (2021.01); *A61B 5/721* (2013.01); *A61B 5/7267* (2013.01); *G06F 3/017* (2013.01)

(58) Field of Classification Search
CPC ......... A61B 5/0531; A61B 5/11; A61B 5/276; A61B 5/369; A61B 5/389; A61B 5/681;
(Continued)

(56) References Cited

U.S. PATENT DOCUMENTS

| 10,299,690 B2 | 5/2019 | Choi et al. |
| 10,786,169 B2 | 9/2020 | Shin et al. |
(Continued)

FOREIGN PATENT DOCUMENTS

| CN | 105845001 A | 8/2016 |
| CN | 114647952 A | 6/2022 |
(Continued)

OTHER PUBLICATIONS

Jack Purcher, "Apple wins a Major Apple Watch Patent that supports Face ID and Sports Performance Analysis via in-band Sensors", Patently Apple, Jun. 29, 2021, 8 pages, url: https://www.patentlyapple.com/2021/06/apple-wins-a-major-apple-watch-patent-that-supports-face-id-and-sports-performance-analysis-via-in-band-sensors.html.

(Continued)

*Primary Examiner* — Richard J Hong
(74) *Attorney, Agent, or Firm* — Sughrue Mion, PLLC

(57) ABSTRACT

A biosignal detection apparatus includes: a sensor unit including a plurality of electrodes configured to obtain a biosignal; memory storing one or more instructions; and one or more processors configured to execute the one or more instructions to: determine a time during which arbitrary electrodes of the plurality of electrodes obtain the biosignal, determine a variability of the biosignal obtained by the (Continued)

arbitrary electrodes, and based on the time during which the arbitrary electrodes obtain the biosignal and the variability of the obtained biosignal satisfying a predetermined reference, determine an arrangement of the arbitrary electrodes and learn the arrangement of the arbitrary electrodes.

19 Claims, 19 Drawing Sheets

(58) Field of Classification Search
CPC ..... A61B 5/7207; A61B 5/721; A61B 5/7267; A61B 5/7455; A61B 5/6826; A61B 5/6898; A61B 5/6841; A61B 5/332; G06F 3/015; G06F 3/017; G06F 3/011; G06V 40/70; G01L 1/146
See application file for complete search history.

(56) References Cited

U.S. PATENT DOCUMENTS

| | | | |
|---|---|---|---|
| 10,874,354 | B2 | 12/2020 | Park et al. |
| 11,045,117 | B2 | 6/2021 | Lor et al. |
| 11,109,773 | B2 | 9/2021 | Urman et al. |
| 12,102,421 | B2 | 10/2024 | Jung et al. |
| 2006/0009691 | A1 | 1/2006 | Yeo et al. |
| 2014/0094675 | A1 | 4/2014 | Luna et al. |
| 2014/0343392 | A1 | 11/2014 | Yang |
| 2016/0192885 | A1* | 7/2016 | Lee ...................... A61B 5/6841 |
| | | | 600/300 |
| 2016/0235341 | A1* | 8/2016 | Choi .................... A61B 5/6898 |
| 2018/0042557 | A1* | 2/2018 | Park ..................... A61B 5/6826 |
| 2018/0317770 | A1* | 11/2018 | Ortega ................... G06F 3/011 |
| 2019/0000354 | A1* | 1/2019 | Lor ......................... G01L 1/146 |
| 2020/0260999 | A1* | 8/2020 | Foxlin ................... G06V 40/70 |
| 2021/0378571 | A1* | 12/2021 | King ..................... A61B 5/332 |
| 2021/0397256 | A1 | 12/2021 | Barachant |
| 2022/0007955 | A1 | 1/2022 | Kang et al. |
| 2022/0249003 | A1 | 8/2022 | Shim et al. |

FOREIGN PATENT DOCUMENTS

| | | |
|---|---|---|
| KR | 10-2016-0100770 A | 8/2016 |
| KR | 10-2016-0105129 A | 9/2016 |
| KR | 10-2018-0017690 A | 2/2018 |
| KR | 10-2003348 B1 | 7/2019 |
| KR | 10-2019-0104036 A | 9/2019 |
| KR | 10-2021-0149375 A | 12/2021 |
| KR | 10-2022-0115084 A | 8/2022 |

OTHER PUBLICATIONS

International Search Report (PCT/ISA/210) issued on Oct. 24, 2023 by the International Searching Authority in International Patent Application No. PCT/KR2023/010295.
Written Opinion (PCT/ISA/237) issued on Oct. 24, 2023 by the International Searching Authority in International Patent Application No. PCT/KR2023/010295.

* cited by examiner

BIO-SIGNAL DETECTION APPARATUS, OPERATING METHOD OF BIO-SIGNAL DETECTION APPARATUS, AND USER TERMINAL COMPRISING BIO-SIGNAL DETECTION APPARATUS CAPABLE OF LEARNING ARRANGEMENT OF BIO-SIGNAL SENSING ELECTRODES

CROSS-REFERENCE TO RELATED APPLICATION

This application is a continuation of International Application No. PCT/KR2023/010295, filed on Jul. 18, 2023, which claims priority to Korean Patent Application No. 10-2022-0113796, filed on Sep. 7, 2022 in the Korean Intellectual Property Office, and Korean Patent Application No. 10-2022-0144621, filed on Nov. 2, 2022 in the Korean Intellectual Property Office the disclosures of which are incorporated by reference herein in their entireties.

BACKGROUND

1. Field

The disclosure relates to a biosignal detection apparatus, an operating method of the biosignal detection apparatus, a user terminal including the biosignal detection apparatus, and a method of determining an arrangement of electrodes to obtain a biosignal.

2. Description of Related Art

In the related art, a method, provided in a user terminal so as to obtain human body signals, includes comparing the sizes of electromyograms, obtained from a plurality of sensors, and obtaining an electromyogram with a larger value as a result of the comparison, or arranging electrodes according to user breathing.

However, related art technologies are not capable of providing the arrangements of electrodes in real time according to a user situation.

SUMMARY

According to an aspect of the disclosure, a biosignal detection apparatus includes: a sensor unit including a plurality of electrodes configured to obtain a biosignal; memory storing one or more instructions; and one or more processors configured to execute the one or more instructions to: determine a time during which arbitrary electrodes of the plurality of electrodes obtain the biosignal, determine a variability of the biosignal obtained by the arbitrary electrodes, and based on the time during which the arbitrary electrodes obtain the biosignal and the variability of the obtained biosignal satisfying a predetermined reference, determine an arrangement of the arbitrary electrodes and learn the arrangement of the arbitrary electrodes.

The one or more processors may be further configured to execute the one or more instructions to determine the variability of the biosignal based on a time during which a waveform of the biosignal obtained by at least one of the arbitrary electrodes is determined to reach a stabilization, and the stabilization of the waveform is determined based on a preset signal-to-noise ratio.

The sensor unit may include a switch unit including a cathode, an anode, and a ground unit, and the one or more processors may be further configured to execute the one or more instructions control connection of at least one of the cathode, the anode, or the ground unit based on the predetermined reference.

The one or more processors may be further configured execute the one or more instructions to: learn the determined arrangement of the arbitrary electrodes based on a preset first deep learning model, and store a learning result of learning the determined arrangement.

The one or more processors may be further configured execute the one or more instructions to: learn first user information including a motion pattern based on a preset second deep learning model, and determine an second electrode arrangement for detecting a biosignal of a second user based on a second learning result of the second deep learning model.

The one or more processors may be further configured to execute the one or more instructions to: update the arrangement of the arbitrary electrodes, and based on determining that the time during which the arbitrary electrodes obtain the biosignal and the variability of the obtained biosignal are equal to or greater than the predetermined reference, obtain a biosignal.

The sensor unit may include a switch unit including a cathode, an anode, and a ground unit, and the one or more processors may be further configured to execute the one or more instructions to: classify a motion of a user, determine the variability of the biosignal based on the motion of the user; and control a connection of at least one of the cathode, the anode, or the ground unit based on a result of the determining the variability of the biosignal based on the motion of the user.

The one or more processors may be further configured to execute the one or more instructions to: determine the variability of the biosignal based on a body part to which the user attaches at least one electrode, and control the connection of the at least one of the cathode, the anode, or the ground unit based on a result of the determining the variability of the biosignal.

The one or more processors may be further configured to execute the one or more instructions to select the arbitrary electrodes that satisfy the predetermined reference from among the plurality of electrodes.

According to an aspect of the disclosure, an operating method of a biosignal detection apparatus including a plurality of electrodes, includes: obtaining a biosignal through arbitrary electrodes of the plurality of electrodes of the biosignal detection apparatus; determining a time during which the arbitrary electrodes obtain the biosignal; determining a variability of the biosignal obtained by the arbitrary electrodes; and based on the time during which the arbitrary electrodes obtain the biosignal and the variability of the obtained biosignal satisfying a predetermined reference, determining an arrangement of the arbitrary electrodes and learning the determined arrangement of the arbitrary electrodes.

The determining the variability of the biosignal obtained by the arbitrary electrodes may include determining the variability of the biosignal based on a time during which a waveform of the biosignal obtained by the arbitrary electrodes is stabilized, and stabilization of the waveform is determined based on a preset signal-to-noise ratio.

The determining and learning the arrangement of the arbitrary electrodes may include controlling connection of at least one of a cathode, an anode, or a ground unit based on the predetermined reference.

The determining and learning the arrangement of the arbitrary electrodes may include learning an arrangement of modeled electrodes based on a preset first deep learning model and storing a learning result.

According to an aspect of the disclosure, a computer-readable recording medium having recorded thereon a program for causing a computer to perform the operating method.

According to an aspect of the disclosure, a user terminal includes: a sensor unit including a plurality of electrodes configured to obtain a biosignal; memory storing one or more instructions; and one or more processors configured to execute the one or more instructions to: determine a time during which arbitrary electrodes of the plurality of electrodes obtain the biosignal, determine a variability of the biosignal obtained by the arbitrary electrodes, and based on the time during which the arbitrary electrodes obtain the biosignal and the variability of the obtained biosignal satisfying a predetermined reference, determine and learn an arrangement of the arbitrary electrodes.

The one or more processors may be further configured to execute the one or more instructions to learn the arrangement of the arbitrary electrodes by setting a function of the user terminal to be controlled based on gesture represented by the biosignal and the arrangement, and the one or more processors may be further configured to execute the one or more instructions to: receive a second biosignal from the sensor unit, and control at least one of an operation of the user terminal or haptic output of the sensor unit based on whether the second biosignal is determined, based on the learned arrangement and the function, to correspond to the gesture.

The sensor unit may be a band worn on a user, the biosignal and the second biosignal may be from the user, and the arrangement may be an arrangement of the any of the plurality of electrodes on a skin of the user.

BRIEF DESCRIPTION OF DRAWINGS

The above and other aspects, features, and advantages of certain embodiments of the present disclosure will be more apparent from the following description taken in conjunction with the accompanying drawings, in which.

DETAILED DESCRIPTION

Figure 1:
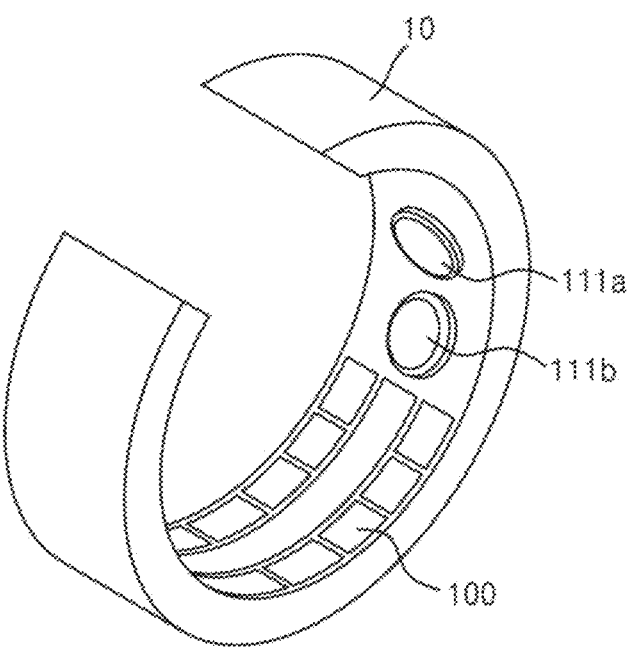
FIG. 1 illustrates a user terminal to which a biosignal detection apparatus according to one or more embodiments is applied.

The terms used in this specification will be briefly explained, and the present disclosure will be described in detail.

The terms used in the present disclosure are selected from the most widely used general terms possible while considering the functions of the present disclosure, but these may vary depending on the intention of technicians in the field, precedents, or the emergence of new technologies. In certain cases, there are terms arbitrarily selected by the applicant, and in such cases, their meanings will be described in detail in the relevant description of the disclosure. Therefore, the terms used in the present disclosure needs to be defined based on the meaning of the terms and the overall content of the present disclosure, rather than simply the names of the terms.

When a certain portion "comprises" or "includes" a certain component throughout the specification, this indicates that the portion may further include another component instead of excluding another component unless otherwise stated. The terms such as "unit" and "module" disclosed in the specification mean units for processing at least one function or operation, which may be implemented by hardware, software, or a combination thereof.

Hereinafter, embodiments are described in detail such that those of ordinary skill in the art may easily implement the same with reference to the accompanying drawings. However, the present disclosure may be implemented in various different forms and is not limited to the embodiments described herein. To clearly explain the present disclosure in the drawings, portions that are not related to the explanation are omitted, and similar portions are given similar drawing reference numerals throughout the specification.

The term "user" in the embodiments of this specification means a person who controls a system, a function, or an operation, and may include a developer, an administrator, or an installer.

In this specification, the "modality" may refer to a sensory channel (e.g., a visual channel, an auditory channel, or a tactile channel) for interaction with a user wearing a wearable device, or a signal, information, or data input and output through the sensory channel. For example, an auditory modality may represent an audio signal output through an auditory channel (e.g., a speaker), a visual modality may represent text, image, or video data output through a visual channel (e.g., a display), and a tactile modality may represent a vibration signal output through a tactile channel (e.g., an actuator).

In this specification, "multi-channel" may include channels separated by the frequency domain. For example, each of a plurality of filters that separate a sound signal into a certain frequency range may correspond to one channel from among multi-channels. Therefore, pulse width modulated (PWM) signals corresponding to the respective filtered signals may be transmitted to the actuator through separate channels. According to an embodiment, one actuator may correspond to one channel.

In this specification, 'neural network' is a representative example of an artificial neural network model that simulates a brain nerve, and is not limited to an artificial neural network model using a certain algorithm.

FIG. 1 illustrates a user terminal 10 to which a biosignal detection apparatus according to one or more embodiments is applied.

The user terminal 10 according to one or more embodiments may include the biosignal detection apparatus and obtain a biosignal of a user. Referring to FIG. 1, a biosignal detection apparatus 100 according to one or more embodiments may be installed in a portion of the user terminal 10, which comes into contact with the wrist of the user, but the location of the biosignal detection apparatus 100 is not limited thereto, and at least one biosignal detection apparatus 100 may be installed in the user terminal 10.

For example, the user terminal 10 may include at least one biosignal detection apparatus 100 and detect the biosignal of the user. The user terminal 10 according to one or more embodiments may include at least one of actuator 111a and actuator 111b. For example, the actuator 111a and actuator 111b may transmit a feedback signal on the biosignal of the user to the user. The number of the actuator 111a and actuator 111b illustrated in FIG. 1 is not limited to two and may further include a plurality of actuators. The user terminal 10 according to one or more embodiments may be a wearable device. The user terminal 10 according to one or more embodiments may be a wrist wearable device. For example, the user terminal 10 according to one or more embodiments may be a band including a bendable material worn on the wrist and coupled to a body of a smart watch or the smart watch.

However, the user terminal 10 is not limited thereto and may include a smart phone, a laptop computer, a tablet PC, a digital camera, an e-book terminal, a digital broadcasting terminal, personal digital assistants (PDA), a portable multimedia player (PMP), a navigation device, and an MP3 player. Hereinafter, one or more embodiments in which a user terminal according to one or more embodiments is a wrist wearable device will be described.

When the biosignal detection apparatus 100 according to one or more embodiments is applied to a wearable device, an electrode may be installed at any location on the wrist of the user. For example, the electrode of the biosignal detection apparatus may be installed on an upper or lower part of the wrist of the user. The electrode of the biosignal detection apparatus 100 according to one or more embodiments may obtain a biosignal and receive a feedback signal of the biosignal detection apparatus 100. Haptic feedback may be provided to the user based on the feedback signal of the biosignal detection apparatus 100. For example, the biosignal detection apparatus 100 may be a universal band that may obtain a biosignal from all parts of the wrist of the user and may perform a control operation on a device connected to an Internet of Things (IoT) device or a metaverse device.

Figure 2:
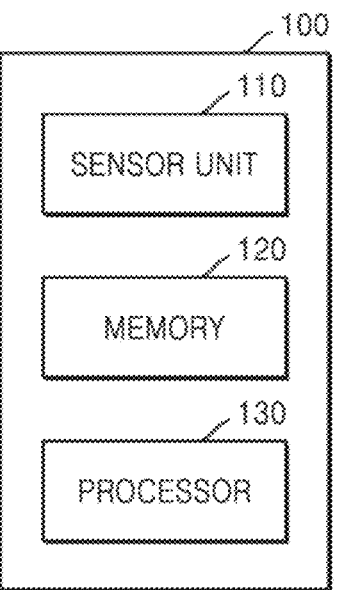
FIG. 2 is a block diagram of a biosignal detection apparatus according to one or more embodiments.

FIG. 2 is a block diagram of the biosignal detection apparatus 100 according to one or more embodiments.

Referring to FIG. 2, the biosignal detection apparatus 100 according to one or more embodiments may include a sensor unit 110, memory 120, or a processor 130.

The sensor unit 110 according to one or more embodiments may include a plurality of electrodes for obtaining a biosignal. For example, the sensor unit 110 may include a plurality of bio-detection sensors, and each of the plurality of bio-detection sensors may include an electrode for obtaining the biosignal. The biosignal according to one or more embodiments may include any biosignal that is to be electrically detected as a signal transmitted through a nerve. For example, the biosignal may include, but is not limited to, a brain wave or an electromyogram. A sensor provided in the sensor unit 110 may include, but is not limited to, an electroencephalogram (EEG) sensor or an electromyography (EMG) sensor. The configuration of the sensor unit 110 is described in detail with reference to FIG. 3.

The memory 120 according to one or more embodiments may include one or more instructions. One or more instructions may include a command for controlling the sensor unit 110. For example, the memory 120 may store a program for an operation of the biosignal detection apparatus 100 and data required therefor. The memory 120 may include a conventional storage medium, for example, a hard disk drive (HDD), read only memory (ROM), random access memory (RAM), flash memory, and a memory card.

One or more processors 130 according to one or more embodiments may execute one or more instructions stored in the memory 120 to determine a time during which arbitrary electrodes of the plurality of electrodes of the sensor unit 110 obtain a biosignal and determine the variability of the biosignal obtained by the arbitrary electrodes. The processor 130 according to one or more embodiments may determine the arrangement of arbitrary electrodes and learn the determined arrangement of the electrodes when the time during which the arbitrary electrodes obtain a biosignal and the variability of the obtained biosignal satisfy a predetermined reference.

For example, the processor 130 may select arbitrary electrodes from among a plurality of electrodes provided in the sensor unit 110 and obtain a biosignal through the selected electrodes. When the biosignal is obtained, the processor 130 may determine whether the obtained biosignal satisfies a preset reference. Whether the obtained biosignal satisfies the preset reference may be determined by comparing a value derived by a function using the time during which the biosignal is obtained or the variability of the biosignal as a variable with $\theta_p$. For example, comparing the preset reference with a value of a biosignal function $F_p$ may be performed using Inequality 1.

$$F_p\left(f_{TR_{ij}}, f_{ID_{ij}}\right) \le \theta_p \qquad \text{<Inequality 1>}$$

Figure 4A:
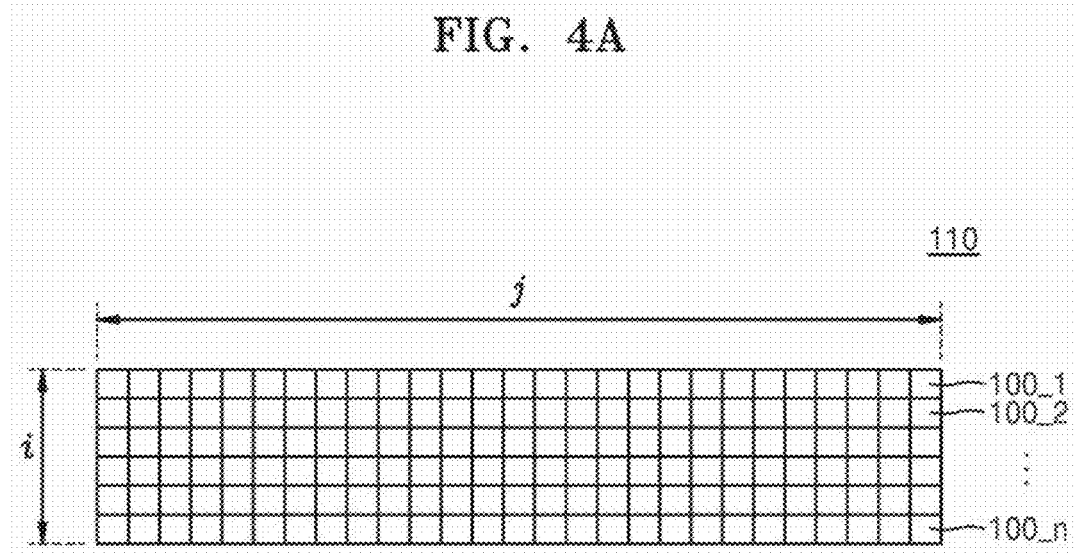
FIG. 4A is a cross-sectional view of a sensor unit according to one or more embodiments.

$f_{RT_{ij}}$ of Inequality 1 according to one or more embodiments may be a time for obtaining a biosignal (response time (RT)) of the sensor unit 110 including i×j electrodes in which the number of electrodes provided in a first direction is i and the number of electrodes provided in a second direction is j, like in FIG. 4A for example. $f_{ID_{ij}}$ of Inequality 1 according to one or more embodiments may be a variability ID of a biosignal obtained by the sensor unit 110 including i×j electrodes in which the number of electrodes provided in the first direction is i and the number of electrodes provided in the second direction is j.

For example, the processor 130 may compare a value of a biosignal function $F_p$ using the $f_{RT_{ij}}$ and $f_{ID_{ij}}$ described above as variables with a preset reference $\theta_p$ and determine and learn, as a valid electrode arrangement, an arrangement of electrodes when the value of the biosignal function is less than or equal to a preset reference $\theta_p$ as the comparison result. The preset reference according to one or more embodiments may be, but is not limited to, a value input by a manufacturer and may be changed by the user. The preset reference may be a value obtained by adjusting a threshold value to match the biosignal characteristics of the user.

The processor 130 according to one or more embodiments may determine a time during which the biosignal is stabilized after being obtained to determine the variability of the obtained biosignal. For example, the processor 130 may determine the variability of the biosignal based on a time during which a waveform of the biosignal obtained by arbitrary electrodes is stabilized and determine stabilization of the waveform based on a preset signal-to-noise ratio (SNR). According to one or more embodiments, the stabilization may be determined based on a preset signal-to-noise ratio (SNR) as in Mathematical Expression 2, and the unit may be decibel (dB).

$$10\log_{10}\left(P_{signal}/P_{noise}\right) \qquad \text{<Mathematical Expression 2>}$$

According to one or more embodiments, $P_{signal}$ of Mathematical Expression 2 may be defined as a size of a biosignal, and $P_{noise}$ may be defined as a size of noise. The processor 130 may determine the variability of the biosignal through a value of Mathematical Expression 2, and when the variability of the biosignal is determined to be less than a preset reference, the biosignal may be determined to be stabilized.

The processor 130 according to one or more embodiments may control components of the sensor unit 110 based on a preset reference $\theta_p$. For example, the processor 130 may control connection of at least one of a cathode, anode, or ground unit of the sensor unit 110 based on a preset reference $\theta_p$. The processor 130 may activate or deactivate an electrode by controlling connection of at least one of the cathode, anode, or ground unit of the sensor unit 110. For example, the processor 130 may determine an electrode arrangement for obtaining a biosignal of a user by controlling activation or deactivation of the electrode.

The processor 130 according to one or more embodiments may learn the determined electrode arrangement based on a preset first deep learning model and store the learning result. By learning and storing the electrode arrangements determined according to a motion, situation, or physical condition of the user, the processor 130 according to one or more embodiments may provide an optimal electrode arrangement according to the condition of the user and accurately obtain the biosignal of the user. The first deep learning model according to one or more embodiments may be a deep learning model that learns electrode arrangements according to the biosignal of the user.

The processor 130 according to one or more embodiments may learn first user information including a motion pattern based on a preset second deep learning model and determine an electrode arrangement for detecting a biosignal of a second user based on the learning result of the second deep learning model. According to one or more embodiments, the first user may refer to a user who is physically different from the second user, and the second deep learning model may be a deep learning model that learns the motion pattern of the user. For example, the processor 130 may learn the motion pattern of the first user and learn the electrode arrangement according to motions of the first user. When the second user performs a motion similar to that of the first user, the processor 130 according to one or more embodiments may provide the second user with the electrode arrangement determined based on a previously learned motion of the first user. However, when obtaining of the biosignal through the electrode arrangement determined based on the motion of the first user is not applied to the second user, the processor 130 may reset an electrode arrangement optimized for the second user.

When determining that the time during which arbitrary electrodes of the sensor unit 110 obtain the biosignal and the variability of the obtained biosignal are greater than or equal to a preset reference $\theta_p$, the processor 130 according to one or more embodiments may update the arrangement of the arbitrary electrodes to obtain a biosignal. For example, when determining that the time during which the arbitrary electrodes obtain the biosignal and the variability of the obtained biosignal are greater than or equal to a preset reference $\theta_p$, the processor 130 may determine that the electrode arrangement provided to the user is not appropriate and change the electrode arrangement to obtain the biosignal again. According to one or more embodiments, the electrode arrangement may be updated through an optimizing process. For example, the processor 130 may perform the optimizing process by selecting, from among the selected arbitrary electrodes, an electrode of which time for obtaining a biosignal satisfies a preset reference and an electrode of which variability of the obtained biosignal satisfies the preset reference and deleting electrodes that do not satisfy the preset reference from the arrangement. The processor 130 according to one or more embodiments may reuse electrodes that satisfy the preset reference to update the arrangement of electrodes without deleting the electrodes from the arrangement.

The processor 130 according to one or more embodiments may generate a feedback signal based on a detection result of the biosignal of the user. For example, when the processor 130 succeeds in detecting the biosignal of the user, the processor 130 may control an actuator to generate a biosignal detection success signal and transmit a feedback signal to the user. When the processor 130 fails to detect the biosignal of the user, the processor 130 may control the actuator to generate a biosignal detection failure signal and transmit a feedback signal to the user. For example, when the processor 130 fails to detect the biosignal of the user, the processor 130 may not perform an optimizing process on an arrangement of electrodes 111 and may control the actuator to generate a biosignal detection failure signal and transmit a feedback signal to the user. The feedback signal according to one or more embodiments may be a vibration signal, but a type of the signal is not limited thereto.

The processor 130 according to one or more embodiments may classify a motion of the user and determine the variability of the biosignal based on the motion of the user. The processor 130 may control connection of at least one of the cathode, anode, or ground unit of the sensor unit 110 based on the determination result of the variability of the biosignal. For example, when the user plays a game of rock-paper-scissors, the processor 130 may classify the motion of the user into a motion of playing scissors, a motion of playing rock, or a motion of playing paper and determine the variability of the biosignal according to the motion of the user. When determining the motion of the user, the processor

130 according to one or more embodiments may provide an arrangement of electrodes according to the motion of the user in real time. However, the classified motion of the user is not limited thereto and may include various motions that the user may physically perform.

The processor 130 according to one or more embodiments may determine the variability of the biosignal based on a body part to which the user attaches at least one electrode. The processor 130 may control connection of at least one of the cathode, anode, or ground unit of the sensor unit 110 based on the determination result of the variability of the biosignal. For example, the user may wear the biosignal detection apparatus 100 on various parts of the body, such as the head, wrist, ankle, thumb, index finger, or middle finger. The processor 130 according to one or more embodiments may learn electrode arrangements according to a location of the user, at which the biosignal detection apparatus 100 is worn, and provide an optimal electrode arrangement according to the location of the user, at which the biosignal detection apparatus 100 is worn.

The processor 130 according to one or more embodiments may select electrodes that satisfy a preset reference $\theta_p$ from among the plurality of electrodes of the sensor unit 110. The processor 130 according to one or more embodiments may reuse electrodes that satisfy the preset reference $\theta_p$ to update the arrangement of the electrodes without deleting the electrodes from the arrangement.

Figure 3:
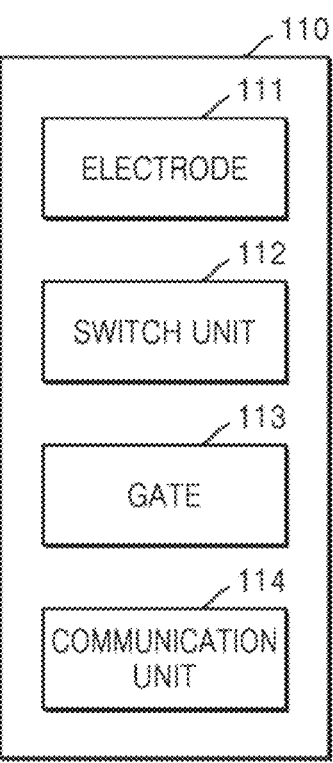
FIG. 3 is a block diagram of a sensor unit according to one or more embodiments.

FIG. 3 is a block diagram of the sensor unit 110 according to one or more embodiments.

Referring to FIG. 3, the sensor unit 110 according to one or more embodiments may include an electrode 111, a switch unit 112, a gate 113, or a communication unit 114.

The electrode 111 according to one or more embodiments may obtain a biosignal. For example, the electrode 111 may detect an electrical signal from a user body and utilize bioimpedance and body information of the user. The electrode 111 according to one or more embodiments may be implemented with a flexible material to be deformed according to a body shape of the user. For example, the electrode 111 may be installed in a wearable device, and the electrode 111 according to one or more embodiments may be installed in a wrist wearable device.

The switch unit 112 may include a cathode, an anode, and a ground unit GND and control an activation state of the electrode by controlling connection of each cathode, anode, or ground unit GND. For example, when the ground unit GND of the switch unit 112 is connected, the corresponding electrode 111 may be deactivated, and when at least one of the cathode or the anode is connected, the corresponding electrode 111 may be activated to obtain a biosignal of the user. The structure of the switch unit 112 is described in detail with reference to FIG. 4A, FIG. 4B, FIG. 4C, and FIG. 5.

The gate 113 may be electrically connected to each electrode 111 to receive a signal for controlling the switch unit 112 and receive or block the biosignal. For example, the gate 113 may be configured to receive, from the processor 130, a signal as to whether to determine a signal obtained by the electrode 111 as a valid signal and receive a biosignal when the signal obtained by the electrode 111 is determined to be a valid signal. The gate 113 may be configured to receive, from the processor 130, the signal as to whether to determine the signal obtained by the electrode 111 as a valid signal and block the biosignal when the signal obtained by the electrode 111 is determined to be an invalid signal. The gate 113 may be provided with, as an interface, an I/O port for connecting human interface devices (HIDs) and an I/O port for input/output of the biosignal.

The communication unit 114 may perform a function of transmitting the biosignal to the processor 130. For example, the communication unit 114 may perform wired or wireless communication with the processor 130 and may communicate with the processor 130 by using Bluetooth communication, Bluetooth low energy (BLE) communication, near field communication unit, wireless local area network (WLAN) (Wi-Fi) communication, Zigbee communication, infrared data association (IrDA) communication, Wi-Fi direct (WFD) communication, ultra wideband (UWB) communication, Ant+ communication, or WIFI communication method, but is not limited thereto.

FIG. 4A is a cross-sectional view of the sensor unit 110 according to one or more embodiments.

Referring to FIG. 4A, the sensor unit 110 according to one or more embodiments may include i×j sensors. For example, when the sensor unit 110 has a square shape and includes i sensors in a first direction and j sensors in a second direction, the sensor unit 110 may include i×j sensors. The sensor unit 110 according to the disclosed embodiment may include a plurality of sensors, such as sensor 110_1, sensor 110_2, through sensor 110_n, and when the number of sensors provided in the sensor unit 110 is i×j, n may be expressed as ij. However, the number of sensors to be provided in the sensor unit 110 and the shape of the sensor unit 110 are not limited thereto, and the sensor unit 110 may include various shapes to be applied to the body of the user.

Figure 4B:
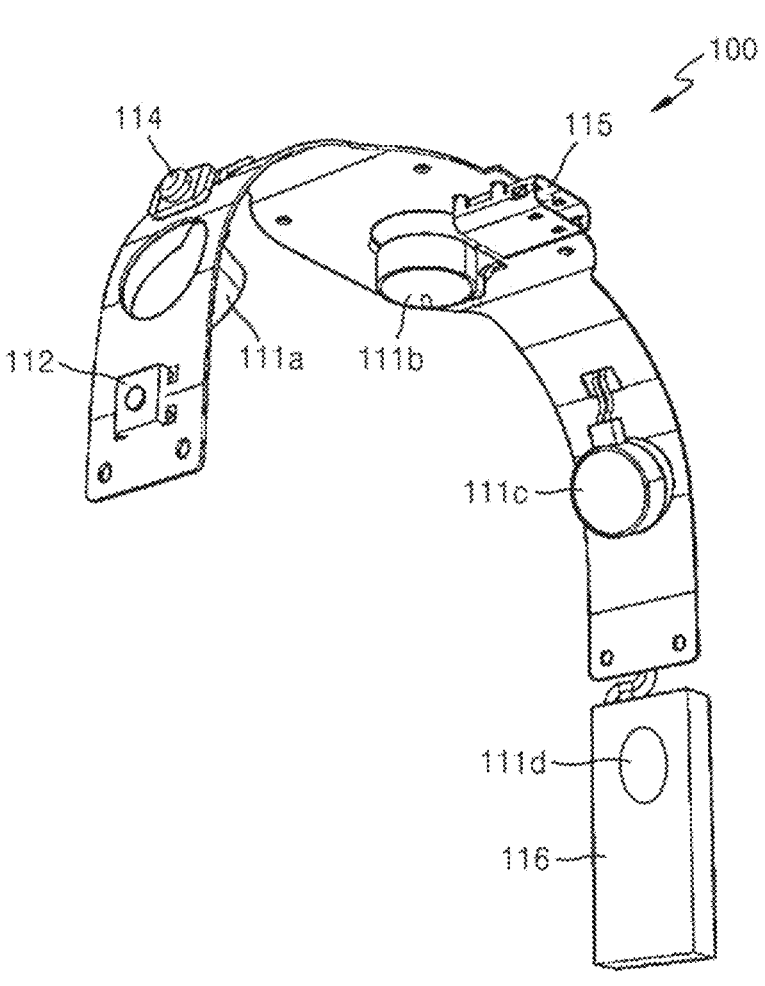
FIG. 4B illustrates structures of a biosignal detection apparatus according to one or more embodiments.
Figure 4C:
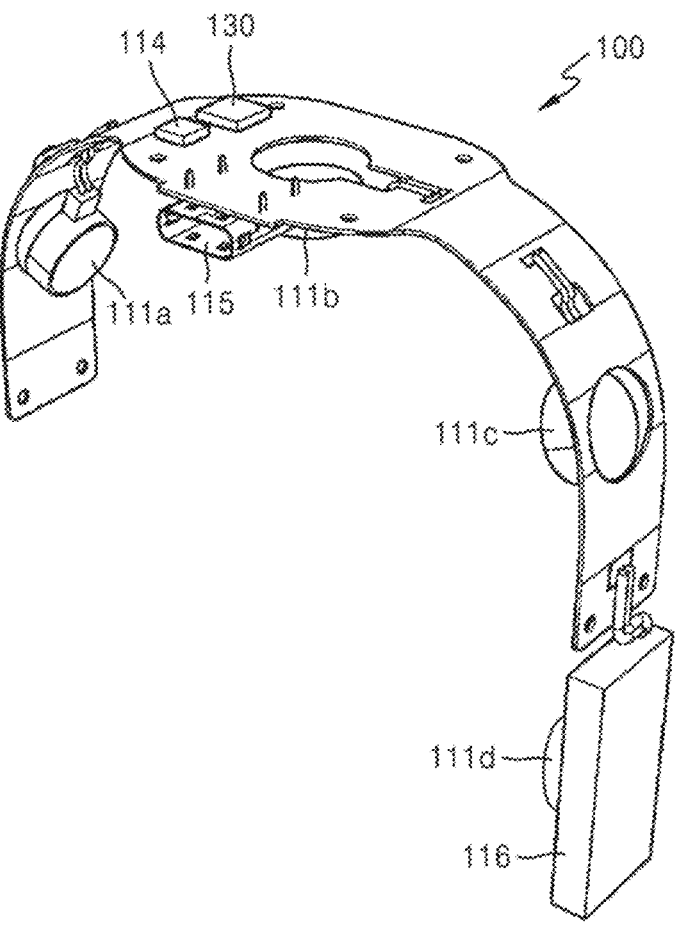
FIG. 4C illustrates structures of a biosignals detection apparatus according to one or more embodiments.

FIG. 4B and FIG. 4C illustrate possible structures of the biosignal detection apparatus 100 according to one or more embodiments. The sensor unit 110 according to one or more embodiments may be present at various locations of the biosignal detection apparatus 100 and may detect the biosignal of the user.

Referring to FIG. 4B, the biosignal detection apparatus 100 may also be implemented in the form of a user terminal. The biosignal detection apparatus 100 according to one or more embodiments may itself be the user terminal 10, and in this case, the processor 130 may control the user terminal 10. The biosignal detection apparatus 100 may also be present as a component of the user terminal 10.

For example, the biosignal detection apparatus 100 may include a plurality of actuators, such as actuator 111a, actuator 111b, actuator 111c, and actuator 111d, the switch unit 112, the communication unit 114, a terminal 115, a battery 116, or the processor 130. However, the present disclosure is not limited thereto, and some components provided in the biosignal detection apparatus 100 may be omitted.

The biosignal detection apparatus 100 according to one or more embodiments may include the plurality of actuators, such as actuator 111a, actuator 111b, actuator 111c, and actuator 111d. Although FIG. 4B and FIG. 4C illustrate merely four actuators, such as actuator 111a, actuator 111b, actuator 111c, and actuator 111d, the number of actuators is not limited thereto.

The actuators, such as actuator 111a, actuator 111b, actuator 111c, and actuator 111d, may be located in direct or indirect contact with the skin of the user (e.g., the skin of a wrist area). Although the shapes of the actuators, such as actuator 111a, actuator 111b, actuator 111c, and actuator 111d, are illustrated as circular, this is merely an example, and the actuators, such as actuator 111a, actuator 111b, actuator 111c, and actuator 111d, may be implemented in various shapes. Although the actuators, such as actuator 111a, actuator 111b, actuator 111c, and actuator 111d, are illustrated as being arranged at regular intervals, this is merely an example, and the actuators, such as actuator 111a, actuator 111b, actuator 111c, and actuator 111d, may be arranged at different intervals or may be arranged connected without gaps.

At least one actuator, such as any of actuator 111a, actuator 111b, actuator 111c, and actuator 111d, according to one or more embodiments may provide feedback on the biosignal detected by the biosignal detection apparatus 100. For example, in a process of sensing the biosignal of the user by the biosignal detection apparatus 100, the actuators, such as actuator 111a, actuator 111b, actuator 111c, and actuator 111d, may provide sensing feedback. The actuators, such as actuator 111a, actuator 111b, actuator 111c, and actuator 111d, according to one or more embodiments may provide feedback on biosignal sensing to the user in the form of vibration.

For example, when succeeding in sensing the biosignal of the user or failing to sense the biosignal of the user, the actuators, such as actuator 111a, actuator 111b, actuator 111c, and actuator 111d, may transmit different vibration signals to the user. When the biosignal detection apparatus 100 is connected to another user device or when a system of the biosignal detection apparatus 100 is upgraded, the actuators, such as actuator 111a, actuator 111b, actuator 111c, and actuator 111d, according to one or more embodiments may provide a success signal of connection with another user device and a success signal of system upgrade to the user in the form of vibration. However, the feedback signal provided by at least one actuator is not limited to a vibration signal and may include various signals such as an air pump signal, an electrical signal, a temperature change signal, or a sound signal.

The switch unit 112 may receive a plurality of signals from the user. For example, when the user inputs a touch signal to the switch unit 112, the user terminal 10 may operate in a biosignal detection mode preset by the user.

The communication unit 114 may be a Bluetooth module, but is not limited thereto. For example, the communication unit 114 may transmit data received by the processor 130 through universal asynchronous receiver/transmitter (UART) communication, but a communication scheme between the communication unit 114 and the processor 130 is not limited thereto.

The terminal 115 may be electrically connected to the battery 116. For example, the terminal 115 may include a universal series bus (USB) jack, but is not limited thereto. The battery 116 may be charged by connecting an external power supply and the battery 116 through the terminal 115.

The battery 116 may supply power to components or circuit elements of a substrate. The battery 116 may be located at one side of the user terminal 10, but the arrangement of the battery 116 is not limited thereto. The battery 116 may be electrically connected to a terminal portion 2127.

The function and operation of the processor 130 are similar to the function and operation of the processor 130 illustrated in FIG. 3, and thus a repeated description is omitted. The processor 130 may control the overall operations of components of the user terminal 10. The processor 130 may process various operations to operate the components of the user terminal 10. For example, the processor 130 may generate a plurality of feedback signals based on data (e.g., biosignal data) obtained from the communication unit 114.

According to one or more embodiments, a tactile modality by a vibration signal may be provided to a user wearing the user terminal 10, along with a visual modality and auditory modality provided from the user terminal 10 or external device(s), thereby providing multimedia immersion through various senses of the user. According to one or more embodiments, a personalized haptic feedback control function may be provided through a user interface, thereby providing a tactile modality that takes into account the characteristics of multimedia data (e.g., music, movies, or games), and the haptic sensitivity and acceptability of the user.

According to one or more embodiments, the personalized haptic feedback control function may be provided through the user interface, and thus an impact point desired by the user from among various characteristics of the multimedia data may be emphasized.

Figure 5:
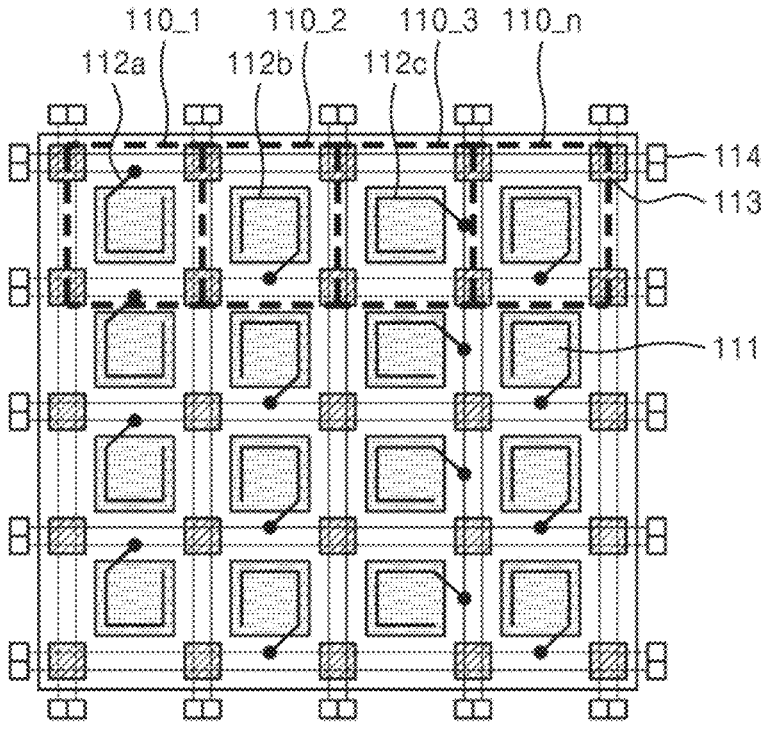
FIG. 5 illustrates a structure of a sensor unit according one or more embodiments.
Figure 6:
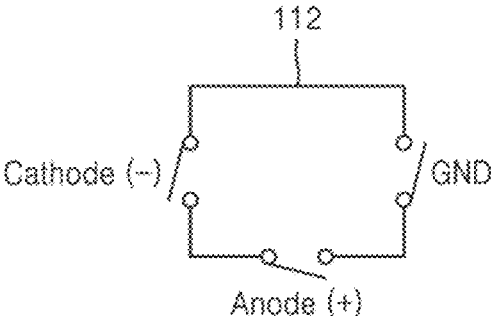
FIG. 6 illustrates a switch of a sensor unit according to one or more embodiments.

FIG. 5 illustrates a structure of the sensor unit 110 according to one or more embodiments, and FIG. 6 illustrates a switch of a sensor unit according to the disclosed embodiment.

Referring to FIG. 5 and FIG. 6, each of the sensors, such as sensor 110_1, sensor 110_2, sensor 110_3, through sensor 110_n, may include the electrode 111, a switch unit 112, such as any of switch unit 112a, switch unit 112b, switch unit 112c, through one or more other switch units, the gate 113, and a signal line 114. Each switch unit 112 may include a cathode switch, an anode switch, and a ground unit GND switch.

As described above, the electrode 111 according to one or more embodiments may obtain a biosignal. For example, the electrode 111 may detect an electrical signal from a user body and utilize bioimpedance and body information of the user. The electrode 111 according to one or more embodiments may be implemented with a flexible material to be deformed according to a body shape of the user.

The switch unit 112 according to one or more embodiments may include a cathode, an anode, and a ground unit GND and control an activation state of the electrode by controlling connection of each cathode, anode, or ground unit GND. For example, when the cathode switch of the switch unit 112 is activated (112a), the electrode 111 may be connected to the signal line 114 that quickly receives a biosignal, and when the ground unit GND switch is activated (112b), the electrode 111 may be connected to the signal line 114 that blocks the biosignal. When the anode switch of the switch unit 112 according to one or more embodiments is activated (112c), the electrode 111 may be connected to the signal line 114, reducing noise of the biosignal, to obtain the biosignal.

Figure 7:
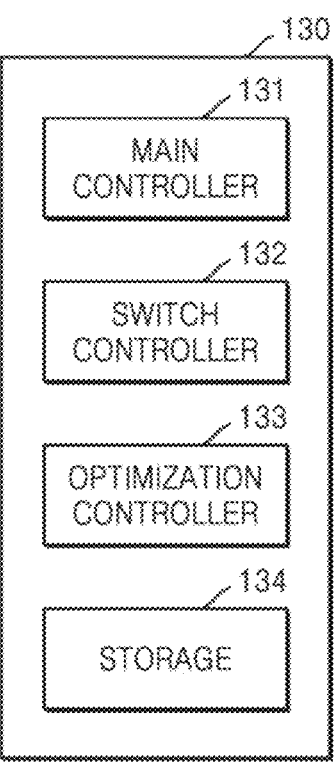
FIG. 7 is a block diagram of a processor according to one or more embodiments.

FIG. 7 is a block diagram of the processor 130 according to one or more embodiments.

Referring to FIG. 7, the processor 130 according to one or more embodiments may include a main controller 131, a switch controller 132, an optimization controller 133, or storage 134.

The main controller 131 according to one or more embodiments may control components of the sensor unit 110 based on a preset reference $\theta_p$. For example, the main controller 131 may generate a plurality of commands to control the switch controller 132 and the optimization controller 133.

The main controller 131 according to one or more embodiments may select arbitrary electrodes from among a plurality of electrodes provided in the sensor unit 110 and obtain a biosignal through the selected electrodes. When the biosignal is obtained, the main controller 131 may determine whether the obtained biosignal satisfies a preset reference. For example, the main controller 131 may compare a value of a biosignal function $F_p$ using $f_{RT_{ij}}$ and $f_{ID_{ij}}$ described above as variables with a preset reference $\theta_p$ and determine and learn, as a valid electrode arrangement, an arrangement of electrodes when the value of the biosignal function $F_p$ is less than or equal to a preset reference $\theta_p$ as the comparison result.

The main controller 131 according to one or more embodiments may determine a time during which the biosignal is stabilized after being obtained to determine the variability of the obtained biosignal. For example, the processor 130 may determine the variability of the biosignal based on a time during which a waveform of the biosignal obtained by arbitrary electrodes is stabilized and determine the stabilization of the waveform based on a preset signal-to-noise ratio (SNR).

The main controller 131 according to one or more embodiments may learn the determined electrode arrangement based on a preset first deep learning model and store the learning result. The main controller 131 according to one or more embodiments may learn first user information including a motion pattern based on a preset second deep learning model and determine an electrode arrangement for detecting a biosignal of a second user based on the learning result of the second deep learning model.

The switch controller 132 according to one or more embodiments may control components of the sensor unit 110 based on a preset reference $\theta_p$. For example, the processor 130 may control connection of at least one of a cathode, anode, or ground unit GND of the sensor unit 110 based on a preset reference $\theta_p$. The switch controller 132 may activate or deactivate the electrode by controlling connection of at least one of the cathode, anode, or ground unit GND of the sensor unit 110. For example, the switch controller 132 may determine an electrode arrangement for obtaining the biosignal of the user by controlling activation or deactivation of the electrode.

The optimization controller 133 according to one or more embodiments may update the arrangement of arbitrary electrodes to obtain a biosignal when determining that the time during which the arbitrary electrodes of the sensor unit 110 obtain the biosignal and the variability of the obtained biosignal are greater than or equal to a preset reference $\theta_p$. For example, when determining that the time during which the arbitrary electrodes obtain the biosignal and the variability of the obtained biosignal are greater than or equal to the preset reference $\theta_p$, the optimization controller 133 may determine that the electrode arrangement provided to the user is not appropriate and change the electrode arrangement to obtain the biosignal again.

According to one or more embodiments, the electrode arrangement may be updated through an optimizing process. For example, the optimization controller 133 may update the electrode arrangement by using regression analysis. That is, the optimization controller 133 may update the electrode arrangement by repeatedly performing a process of selecting a valid electrode. The optimization controller 133 according to one or more embodiments may perform the optimizing process by selecting, from among the selected arbitrary electrodes, an electrode of which time for obtaining a biosignal satisfies a preset reference and an electrode of which variability of the obtained biosignal satisfies the preset reference and deleting electrodes that do not satisfy the preset reference from the arrangement. The processor 130 according to one or more embodiments may reuse electrodes that satisfy the preset reference to update the arrangement of electrodes without deleting the electrodes from the arrangement.

The storage 134 according to one or more embodiments may store the result of learning performed by the processor 130. For example, the storage 134 may learn the electrode arrangement determined by the main controller 131 based on a preset first deep learning model and store the learning result. The main controller 131 according to one or more embodiments may learn first user information including a motion pattern based on a preset second deep learning model and store the learning result of the second deep learning model in the storage 134. However, data to be stored in the storage 134 is not limited thereto, and various information generated by the processor 130 may be stored.

Figure 8:
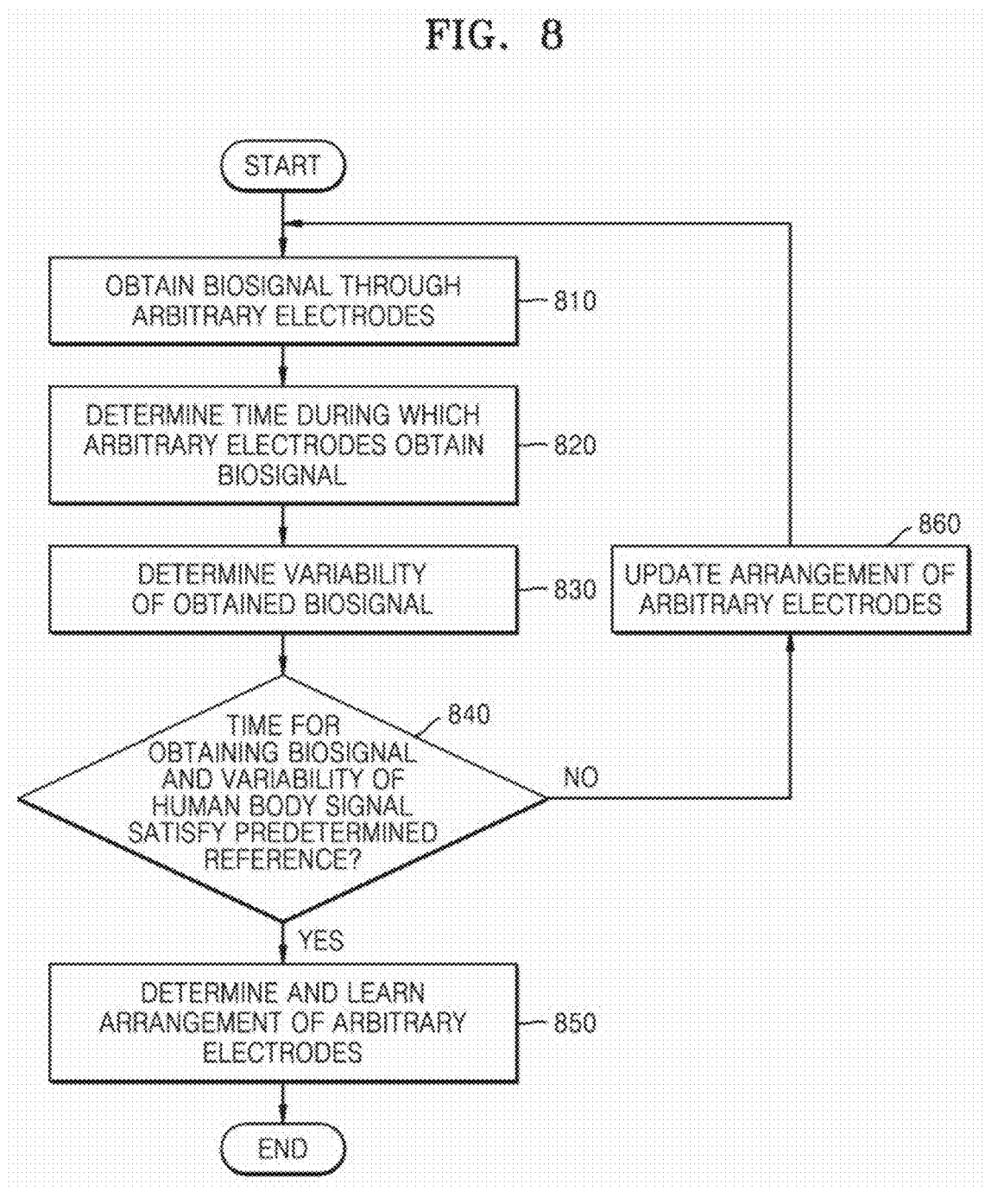
FIG. 8 is a flowchart of an operation method of a biosignal detection apparatus according to one or more embodiments.

FIG. 8 is a flowchart of an operation method of the biosignal detection apparatus 100 according to one or more embodiments.

Referring to FIG. 8, the biosignal detection apparatus 100 according to one or more embodiments may obtain a biosignal through arbitrary electrodes (810). For example, the biosignal detection apparatus 100 may obtain the biosignal by changing arbitrary electrodes present in the sensor unit 110 in real time.

When the biosignal is obtained through arbitrary electrodes, the biosignal detection apparatus 100 may determine a time during which the arbitrary electrodes obtain the biosignal (820). The biosignal detection apparatus 100 according to one or more embodiments may utilize the time for obtaining the biosignal as a first variable of Inequality 1. For example, when determining that the time for obtaining the biosignal is equal to or less than a preset reference, the biosignal detection apparatus 100 may determine a corresponding electrode as a valid electrode.

When determining the time for obtaining the biosignal, the biosignal detection apparatus 100 may determine the variability of the obtained biosignal (830). The biosignal detection apparatus 100 according to one or more embodiments may determine a time during which the biosignal is stabilized after being obtained to determine the variability of the obtained biosignal. For example, the biosignal detection apparatus 100 may determine the variability of the biosignal based on the time during which a waveform of the biosignal obtained by arbitrary electrodes is stabilized and determine the stabilization of the waveform based on a preset signal-to-noise ratio (SNR). According to one or more embodiments, the stabilization may be determined by a preset signal-to-noise ratio (SNR) as in Mathematical Expression 2, and the unit may be decibel (dB).

When determining the variability of the biosignal, the biosignal detection apparatus 100 may determine whether the time for obtaining the biosignal and the variability of a human body signal satisfy a preset reference (840). When a preset reference is defined as $\theta_p$, whether the obtained biosignal satisfies the preset reference may be determined by comparing a value derived by a function using the time during which the biosignal is obtained or the variability of the biosignal as a variable with $\theta_p$. For example, comparing the value of a biosignal function $F_p$ with a preset reference may be performed using Inequality 1.

When determining that the time for obtaining the biosignal and the variability of the human body signal satisfy the preset reference, the biosignal detection apparatus 100 may determine and learn an arrangement of arbitrary electrodes (850).

However, when determining that the time for obtaining the biosignal and the variability of the human body signal do not satisfy the preset reference, the biosignal detection apparatus 100 may update the arrangement of the arbitrary electrodes (860). For example, the biosignal detection apparatus 100 may update the arrangement of the arbitrary electrodes through an optimizing process. The biosignal detection apparatus according to one or more embodiments may perform the optimizing process by selecting, from among the selected arbitrary electrodes, an electrode of which time for obtaining a biosignal satisfies a preset reference and an electrode of which variability of the obtained biosignal satisfies the preset reference and deleting electrodes that do not satisfy the preset reference from the arrangement.

Figure 9:
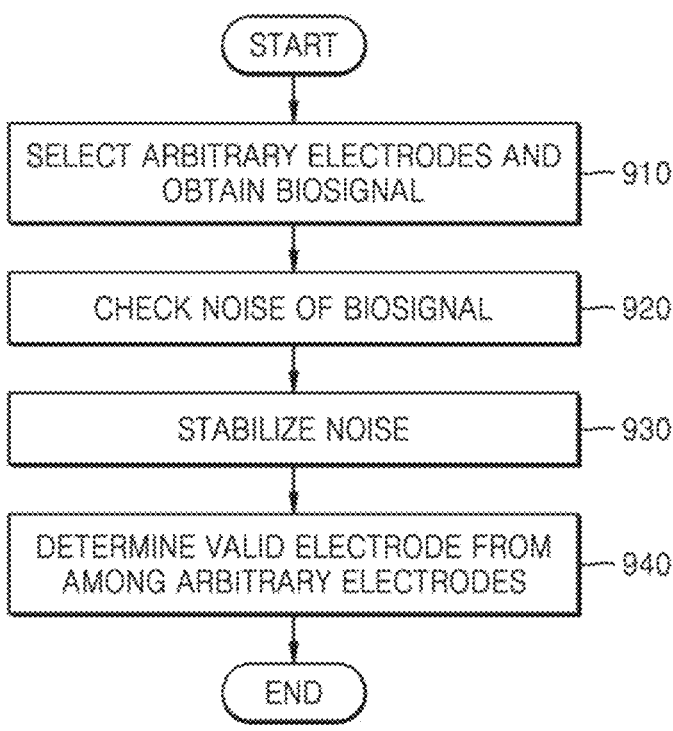
FIG. 9 is a flowchart of a process of selecting an arbitrary electrode in an operating method of a biosignal detection apparatus according to one or more embodiments.

FIG. 9 is a flowchart of a process of selecting an arbitrary electrode in an operating method of the biosignal detection apparatus 100 according to one or more embodiments.

Referring to FIG. 9, the biosignal detection apparatus 100 according to one or more embodiments may obtain a bio-signal through arbitrary electrodes (910).

When obtaining the biosignal, the biosignal detection apparatus 100 according to one or more embodiments may check noise contained in the biosignal (920). For example, the biosignal detection apparatus 100 may classify a signal other than the biosignal provided in the obtained signal.

When noise in the biosignal is confirmed, the biosignal detection apparatus 100 according to one or more embodiments may stabilize the noise (930). For example, the biosignal detection apparatus 100 may remove noise by stabilizing a biosignal waveform. The biosignal detection apparatus 100 according to one or more embodiments may determine the variability of the biosignal based on a time during which a waveform of the biosignal obtained by arbitrary electrodes is stabilized and determine the stabili-zation of the waveform based on a preset signal-to-noise ratio (SNR). The stabilization according to one or more embodiments may be determined by a preset signal-to-noise ratio (SNR) as in Mathematical Expression 2, and the unit may be decibel (dB).

When determining that the noise is stabilized, the biosig-nal detection apparatus 100 according to one or more embodiments may determine a valid electrode from among arbitrary electrodes (940). For example, the biosignal detec-tion apparatus 100 may determine, as valid electrode, elec-trodes in which noise stabilizes below a preset reference and learn an arrangement of the valid electrodes. The valid electrode may be an electrode that is activated in obtaining a biosignal.

Figure 10A:
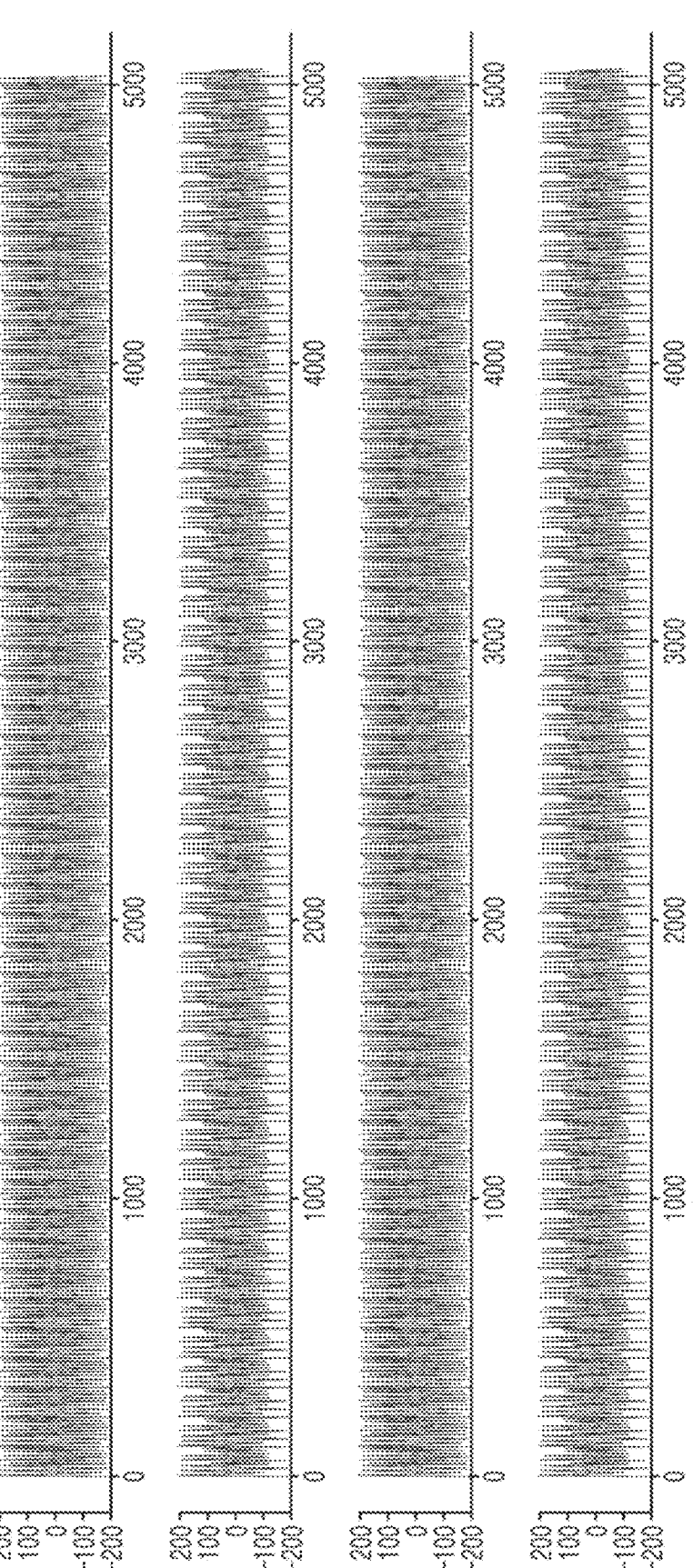
FIGS. 10A to 10C illustrate stabilization of a biosignal obtained by a biosignal detection apparatus according to one or more embodiments.
Figure 10B:
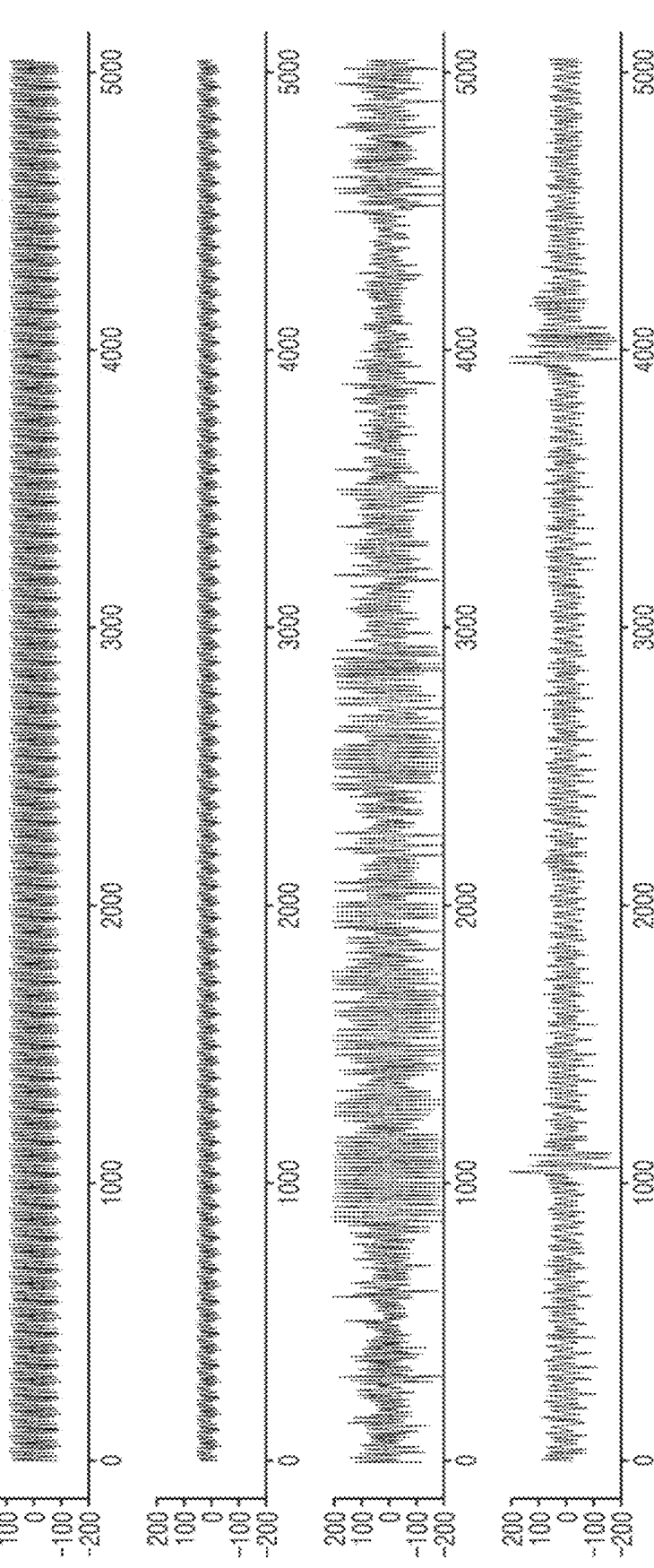
Figure 10C:
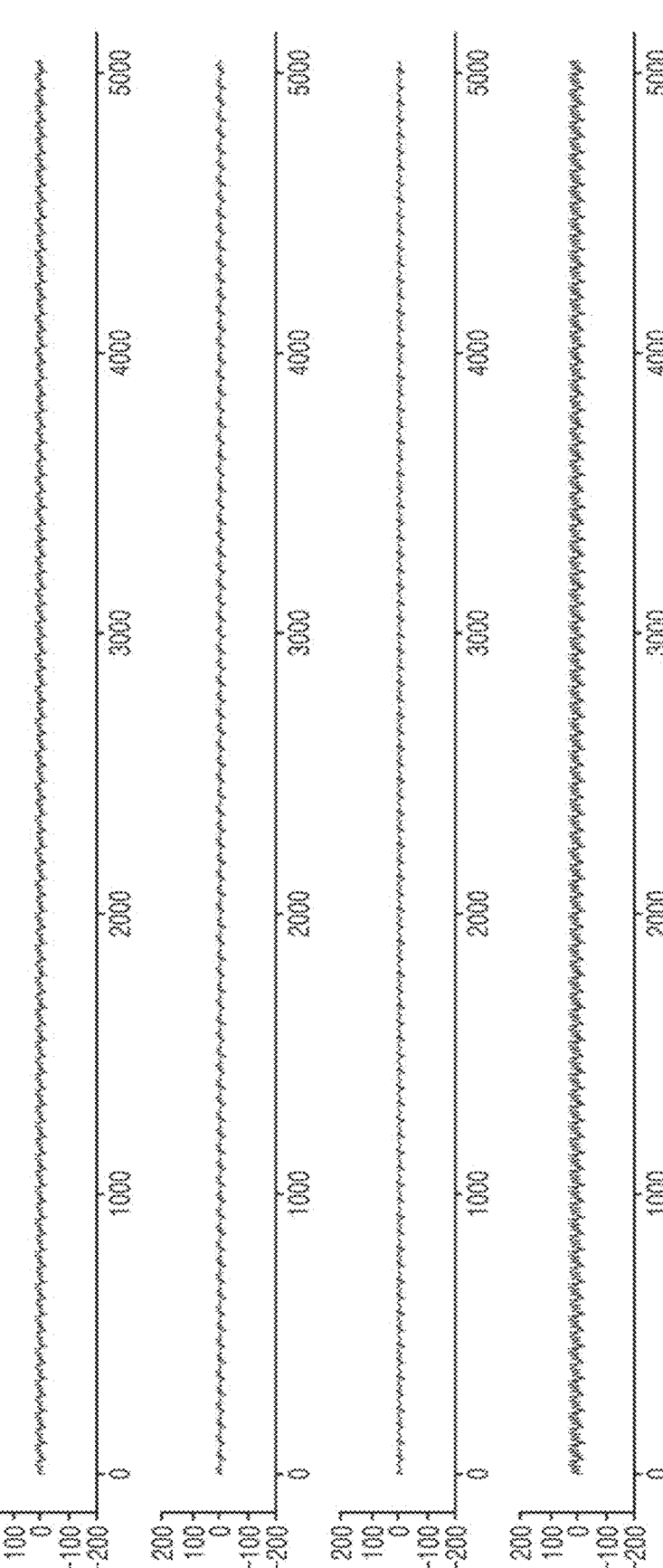

FIG. 10A, FIG. 10B, and FIG. 10C illustrate stabilization of a biosignal obtained by the biosignal detection apparatus 100 according to one or more embodiments.

The x-axis in FIG. 10A, FIG. 10B, and FIG. 10C repre-sents a time for obtaining a signal, and the y-axis represents a size of noise of the signal. Although the noise of the biosignal according to the disclosed embodiment is expressed by first to fourth waveforms, it is obvious that the noise of the biosignal may contain noise in more waveforms depending on a location of the user, at which the biosignal detection apparatus 100 is worn.

FIG. 10A illustrates a waveform of a signal received when the biosignal detection apparatus 100 according to one or more embodiments is not in contact with the skin of the user. When a biosignal is not received, the signal received by the biosignal detection apparatus 100 contains noise in many waveforms.

FIG. 10B illustrates a waveform of a signal at a time point at which the biosignal detection apparatus 100 according to one or more embodiments is in contact with the skin of the user and receives a biosignal. When the biosignal begins to be received, the signal received by the biosignal detection apparatus 100 has a waveform with stabilized noise or irregular noise depending on the location of the user, at which the biosignal detection apparatus 100 is worn.

FIG. 10C illustrates a waveform of a signal after the biosignal detection apparatus 100 according to one or more embodiments is in contact with the skin of the user and a stabilization operation is performed. When noise in the biosignal is checked, the biosignal detection apparatus 100 according to one or more embodiments may stabilize the noise. For example, the biosignal detection apparatus 100 may remove noise by stabilizing a biosignal waveform.

Figure 11:
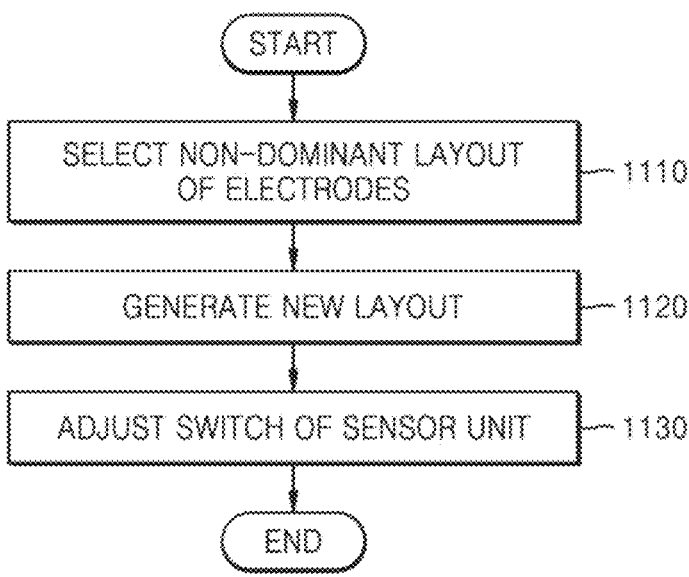
FIG. 11 is a flowchart of a process of selecting an arbitrary electrode in an operating method of a biosignal detection apparatus according to one or more embodiments.

FIG. 11 is a flowchart of a process of selecting an arbitrary electrode in an operating method of a biosignal detection apparatus according to one or more embodiments.

Referring to FIG. 11, the biosignal detection apparatus 100 according to one or more embodiments may select a non-dominant layout of electrodes (1110). The non-domi-nant layout of electrodes according to one or more embodi-ments may mean a layout of electrodes having a shorter time for obtaining a biosignal than a preset reference and elec-trodes having lower variability than the preset reference. For example, the biosignal detection apparatus 100 may deter-mine the non-dominant layout as an arrangement of elec-trodes that satisfy the preset reference and determine the non-dominant layout as an arrangement of valid electrodes.

When the non-dominant layout is selected, the biosignal detection apparatus 100 according to one or more embodi-ments may generate a new layout (1120). For example, the biosignal detection apparatus 100 may generate a new layout including electrodes of the non-dominant layout and deter-mine whether the generated new layout satisfies the preset reference.

When the new layout is generated, the biosignal detection apparatus 100 according to one or more embodiments may adjust switches of the sensor unit 110 (1130). For example, to determine whether the new layout satisfies the preset reference and determine a valid electrode, the biosignal detection apparatus 100 may activate or deactivate an elec-trode by controlling connection of at least one of the cathode, anode, or ground unit GND of the sensor unit 110. By controlling activation of the electrodes, the biosignal detection apparatus 100 according to one or more embodi-ments may determine and learn new electrode arrangements to be applied depending on a motion and state of the user.

Figure 12:
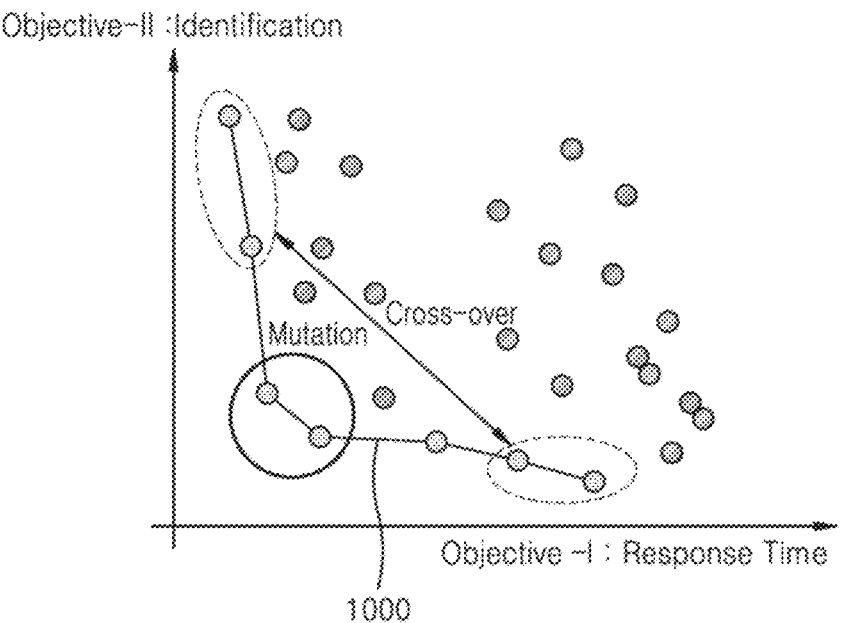
FIG. 12 is diagram for explaining optimization of biosignal data according to one or more embodiments.

FIG. 12 is diagram for explaining optimization of biosig-nal data according to one or more embodiments.

The x-axis of FIG. 12 may represent a time (response time) to obtain a biosignal from each electrode, and the y-axis may represent the consistency of the obtained bio-signal.

Referring to FIG. 12, the biosignal detection apparatus 100 according to one or more embodiments may determine electrodes having a shorter time for obtaining a biosignal than a preset reference and electrodes having lower vari-ability than the preset reference as valid electrodes (1000). The biosignal detection apparatus 100 according to one or more embodiments may remove signal noise by cross-overing signals of electrodes having a shorter time for obtaining the biosignal than the preset reference and but a high variability of the obtained signal and electrodes having a lower variability than the preset reference but a relatively long time for obtaining the biosignal. The biosignal detec-tion apparatus 100 according to one or more embodiments may immediately determine, as valid electrodes, electrodes (mutations) having a shorter time for obtaining the biosignal than the preset reference and a lower variability than the preset reference.

Figure 13:
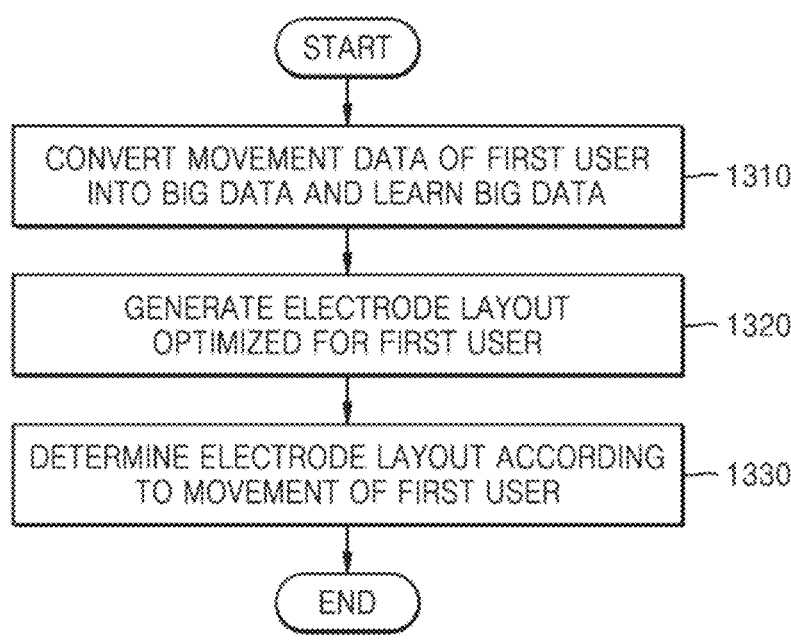
FIG. 13 is a flowchart of a process of determining a layout of electrodes in a biosignal detection apparatus according to one or more embodiments.

FIG. 13 is a flowchart of a process of determining a layout of electrodes in a biosignal detection apparatus according to one or more embodiments.

Referring to FIG. 13, the biosignal detection apparatus 100 according to one or more embodiments may convert movement data of a first user into big data and learn the big data (1310). For example, the biosignal detection apparatus 100 may obtain a biosignal that varies according to a motion of a user and convert the obtained biosignal into big data and store the big data.

When the movement data of the first user is converted into big data and learned, the biosignal detection apparatus 100 according to one or more embodiments may generate an electrode layout optimized for the first user (1320). For example, the biosignal detection apparatus 100 may match a motion of the first user with a corresponding biosignal and learn the matching result and match the generated layouts with the motion of the user and store the matching result.

When the electrode layout optimized for the first user is generated, the biosignal detection apparatus 100 according to one or more embodiments may determine the layout of electrodes according to the movement of the first user (1330). For example, when the first user repeats a previously performed motion, the biosignal detection apparatus 100 may provide the first user with an electrode arrangement according to a pre-stored motion without newly determining the time for obtaining the biosignal and the variability of the biosignal. The biosignal detection apparatus 100 according to one or more embodiments may provide the second user with the electrode arrangement according to the pre-stored motion when the second user performs the same motion as the first user. By converting the electrode arrangement according to a motion of the user into big data, the biosignal detection apparatus 100 according to one or more embodiments may have an effect of accurately and quickly obtaining the biosignal of the user.

Figure 14:
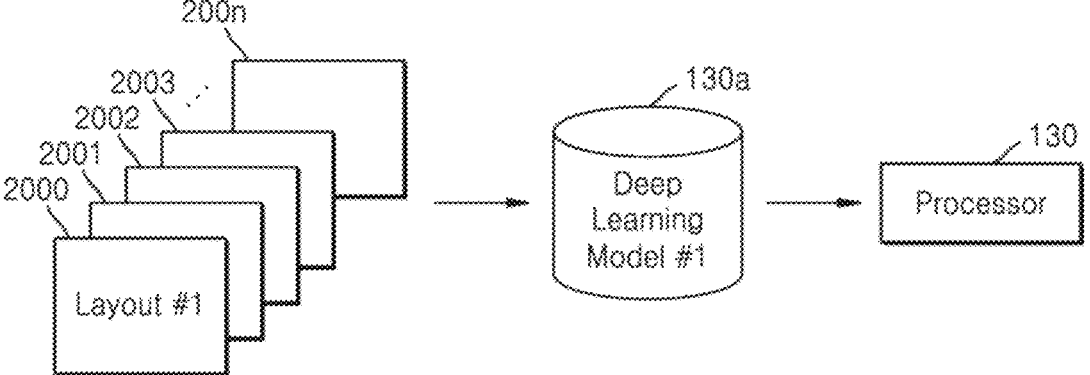
FIG. 14 is a diagram for explaining a case in which a biosignal detection apparatus according to one or more embodiments learns a layout of arbitrary electrodes.

FIG. 14 is a diagram for explaining a case in which a biosignal detection apparatus according to one or more embodiments learns a layout of arbitrary electrodes.

Referring to FIG. 14, the biosignal detection apparatus 100 according to one or more embodiments may convert a plurality of electrode arrangements, such as layout 2000, layout 2001, layout 2002, layout 2003, through layout 200n, determined according to the motion or state of the user into big data and store and learn the big data. For example, the biosignal detection apparatus 100 may learn the plurality of electrode arrangements, such as layout 2000, layout 2001, layout 2002, layout 2003, through layout 200n, by a first deep learning model 130a. The biosignal detection apparatus 100 according to one or more embodiments may store the electrode arrangements, such as layout 2000, layout 2001, layout 2002, layout 2003, through layout 200n, according to the motion or state of the user, and the processor 130 may provide the pre-stored electrode arrangements when the first user or the second user performs a pre-stored motion based on the learning result.

Figure 15:
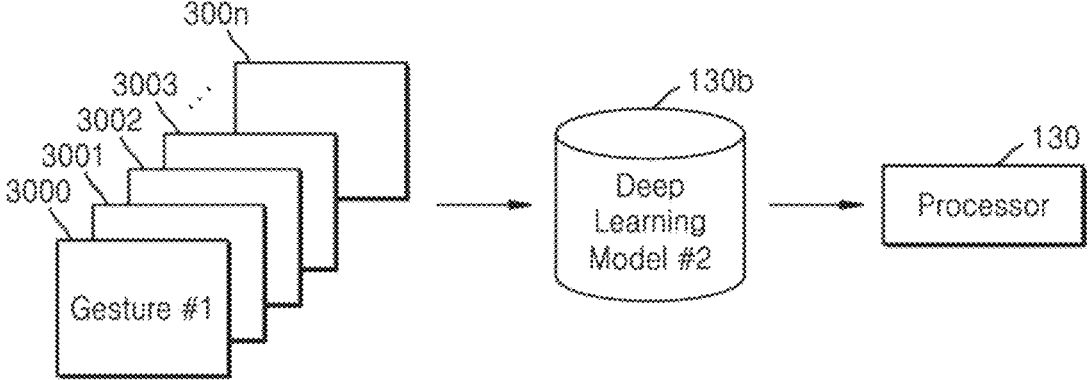
FIG. 15 is a diagram for explaining a case in which a biosignal detection apparatus according to one or more embodiments learns a motion of a user.

FIG. 15 is a diagram for explaining a case in which a biosignal detection apparatus according to one or more embodiments learns a motion of a user.

Referring to FIG. 15, the biosignal detection apparatus 100 according to one or more embodiments may convert user motions 3000, 3001, 3002, 3003, through 300n into big data and store and learn the big data. For example, the biosignal detection apparatus 100 may learn the user motions, such as gesture 3000, gesture 3001, gesture 3002, gesture 3003, through gesture 300n, by a second deep learning model 130b. The biosignal detection apparatus 100 according to one or more embodiments may store the user motions, such as gesture 3000, gesture 3001, gesture 3002, gesture 3003, through gesture 300n, and the processor 130 may provide the pre-stored electrode arrangements when the first user or the second user performs a pre-stored motion based on the learning result.

The biosignal detection apparatus 100 according to the disclosed embodiment may include the sensor unit 110 including a plurality of electrodes for obtaining a biosignal, the memory 120 including one or more instructions, and the one or more processors 130.

The one or more processors 130 according to one or more embodiments may execute one or more instructions to determine a time during which arbitrary electrodes of a plurality of electrodes obtain a biosignal.

The one or more processors 130 according to one or more embodiments may determine the variability of the biosignal obtained by the arbitrary electrodes.

The one or more processors 130 according to one or more embodiments may determine the arrangement of arbitrary electrodes and learn the determined arrangement of the electrodes when the time during which the arbitrary electrodes obtain a biosignal and the variability of the obtained biosignal satisfy a predetermined reference.

The one or more processors 130 according to one or more embodiments may determine the variability of the biosignal based on a time during which a waveform of the biosignal obtained by arbitrary electrodes is stabilized and determine the stabilization of the waveform based on a preset signal-to-noise ratio (SNR).

The sensor unit 110 according to one or more embodiments may include the switch unit 112 including the cathode, the anode, and the ground unit GND.

The one or more processors 130 according to one or more embodiments may control connection of at least one of the cathode, the anode, or the ground unit based on a predetermined reference.

The one or more processors 130 according to one or more embodiments may learn the determined electrode arrangement based on a preset first deep learning model and store the learning result.

The one or more processors 130 according to one or more embodiments may learn first user information including a motion pattern based on a preset second deep learning model and determine an electrode arrangement for detecting a biosignal of a second user based on the learning result of the second deep learning model.

The one or more processors 130 according to one or more embodiments may update the arrangement of arbitrary electrodes to obtain a biosignal when determining that the time during which arbitrary electrodes obtain the biosignal and the variability of the obtained biosignal are greater than or equal to a predetermined reference.

The one or more processors 130 according to one or more embodiments may classify a user motion, determine the variability of a biosignal based on the user motion, and control connection of at least one of the cathode, the anode, or the ground unit based on the determination result.

The one or more processors 130 according to one or more embodiments may determine the variability of the biosignal based on a body part to which the user attaches at least one electrode and control connection of at least one of the cathode, the anode, or the ground unit based on the determination result.

The one or more processors 130 according to one or more embodiments may select electrodes that satisfy a preset reference from among a plurality of electrodes.

An operating method of the biosignal detection apparatus 100 including a plurality of electrodes according to one or more embodiments may include obtaining a biosignal through arbitrary electrodes (810), determining a time during which the arbitrary electrodes obtain the biosignal (820), determining a variability of the biosignal obtained by the arbitrary electrodes (830), and determining and learning an arrangement of the arbitrary electrodes when the time during which the arbitrary electrodes obtain the biosignal and the variability of the obtained biosignal satisfy a predetermined reference (850).

The determining of the variability of the biosignal obtained by the arbitrary electrodes (830) according to one or more embodiments may include determining the variability of the biosignal based on the time during which a waveform of the biosignal obtained by the arbitrary electrodes is stabilized, and in this case, the stabilization of the waveform may be determined based on a preset signal-to-noise ratio (SNR).

The determining and learning of the arrangement of the arbitrary electrodes (850) according to one or more embodiments may include controlling connection of at least one of a cathode, anode, or ground unit of the sensor unit 110 based on a predetermined reference.

The determining and learning of the arrangement of the arbitrary electrodes (850) according to one or more embodiments may include learning an arrangement of modeled electrodes based on a preset first deep learning model and storing the learning result.

The determining and learning of the arrangement of the arbitrary electrodes (850) according to one or more embodiments may include learning first user information including a motion pattern based on a preset second deep learning model and determining an electrode arrangement for detecting a biosignal of a second user based on the learning result of the second deep learning model.

The obtaining of the biosignal through the arbitrary electrodes according to one or more embodiments (810) according to one or more embodiments may include optimizing the arrangement of the arbitrary electrodes and obtaining the biosignal when determining that the time during which the arbitrary electrodes obtain the biosignal and the variability of the obtained biosignal are equal to or less than a predetermined reference.

The determining and learning of the arrangement of the arbitrary electrodes (850) according to one or more embodiments may include classifying a user motion, determining the variability of a biosignal based on the user motion, and controlling connection of at least one of the cathode, the anode, or the ground unit based on the determination result.

The determining and learning of the arrangement of the arbitrary electrodes (850) according to one or more embodiments may include determining the variability of the biosignal based on a body part to which the user attaches at least one electrode and controlling connection of at least one of the cathode, the anode, or the ground unit based on the determination result.

The determining and learning of the arrangement of the arbitrary electrodes (850) according to one or more embodiments may include selecting electrodes that satisfy a preset reference from among a plurality of electrodes.

According to one or more embodiments, a computer-readable recording medium having a program recorded thereon may store a program for causing a computer to perform the biosignal detection method described above.

The user terminal 10 according to the disclosed embodiment may include the sensor unit 110 including a plurality of electrodes for obtaining a biosignal, the memory 120 including one or more instructions, and the one or more processors 130, and the one or more processors 130 may execute the one or more instructions.

The one or more processors 130 according to one or more embodiments may determine the time during which arbitrary electrodes of the plurality of electrodes obtain the biosignal and determine the variability of the biosignal obtained by the arbitrary electrodes.

The one or more processors 130 according to one or more embodiments may determine and learn the arrangement of arbitrary electrodes when the time during which arbitrary electrodes obtain a biosignal and the variability of the obtained biosignal satisfy a predetermined reference.

A device-readable storage medium may be provided in the form of a non-transitory storage medium. Here, the term 'non-transitory storage medium' simply means a tangible device that does not contain a signal (e.g. electromagnetic wave), and the term does not distinguish between cases in which data is stored semi-permanently or temporarily on a storage medium. For example, the 'non-transitory storage medium' may include a buffer in which data is temporarily stored.

According to one or more embodiments, the methods according to various embodiments disclosed in the present specification may be provided as provided in a computer program product. The computer program product may be traded between a seller and a buyer as a commodity. The computer program product may be distributed in the form of a machine-readable storage medium (e.g., compact disc read only memory (CD-ROM)), or may be distributed online (e.g., by download or upload) via an application store or directly between two user devices (e.g., smartphones). In the case of online distribution, at least a portion of the computer program product (e.g., a downloadable app) may be temporarily stored or temporarily generated in a device-readable storage medium, such as memory of a server of a manufacturer, server of an application store, or intermediary server.

What is claimed is:

1. A biosignal detection apparatus comprising:
   a sensor unit comprising a plurality of electrodes configured to obtain a biosignal;
   memory storing one or more instructions; and
   one or more processors configured to execute the one or more instructions to:
       determine, based on a number of arbitrary electrodes of the sensor unit, a response time (RT) during which the arbitrary electrodes of the plurality of electrodes obtain the biosignal,
       based on identifying a time within a period of the RT during which a waveform of the biosignal obtained by at least one of the arbitrary electrodes is determined to reach a stabilization, determine a variability of the biosignal obtained by the arbitrary electrodes, and
       based on the RT during which the arbitrary electrodes obtain the biosignal and the variability of the obtained biosignal satisfying a predetermined reference, determine an arrangement of the arbitrary electrodes and learn the arrangement of the arbitrary electrodes.

2. The biosignal detection apparatus of claim 1, wherein the one or more processors are further configured to execute the one or more instructions to determine the stabilization of the waveform based on a preset signal-to-noise ratio.

3. The biosignal detection apparatus of claim 1, wherein the sensor unit comprises a switch unit comprising a cathode, an anode, and a ground unit, and wherein the one or more processors are further configured to execute the one or more instructions to control connection of at least one of the cathode, the anode, or the ground unit based on the predetermined reference.

4. The biosignal detection apparatus of claim 1, wherein the one or more processors are further configured execute the one or more instructions to:

learn the determined arrangement of the arbitrary electrodes based on a preset first deep learning model, and store a learning result of learning the determined arrangement.

5. The biosignal detection apparatus of claim 4, wherein the one or more processors are further configured execute the one or more instructions to:

learn first user information including a motion pattern based on a preset second deep learning model, and determine a second electrode arrangement for detecting a biosignal of a second user based on a second learning result of the preset second deep learning model.

6. The biosignal detection apparatus of claim 1, wherein the one or more processors are further configured to execute the one or more instructions to:

update the arrangement of the arbitrary electrodes, and based on determining that the RT during which the arbitrary electrodes obtain the biosignal and the variability of the obtained biosignal are equal to or greater than the predetermined reference, obtain a second biosignal.

7. The biosignal detection apparatus of claim 1, wherein the sensor unit comprises a switch unit comprising a cathode, an anode, and a ground unit, and wherein the one or more processors are further configured to execute the one or more instructions to:

classify a motion of a user, determine the variability of the biosignal based on the motion of the user; and control a connection of at least one of the cathode, the anode, or the ground unit based on a result of the determining the variability of the biosignal based on the motion of the user.

8. The biosignal detection apparatus of claim 7, wherein the one or more processors are further configured to execute the one or more instructions to:

determine the variability of the biosignal based on a body part to which the user attaches at least one electrode, and control the connection of the at least one of the cathode, the anode, or the ground unit based on the result of the determining the variability of the biosignal.

9. The biosignal detection apparatus of claim 1, wherein the one or more processors are further configured to execute the one or more instructions to select the arbitrary electrodes that satisfy the predetermined reference from among the plurality of electrodes.

10. The biosignal detection apparatus of claim 1, wherein determining the RT during which the arbitrary electrodes of the plurality of electrodes obtain the biosignal is further based on a first number of arbitrary electrodes along at least one direction of the sensor unit, and a second number of arbitrary electrodes along a second direction of the sensor unit, the second direction is perpendicular to the at least one direction.

11. The biosignal detection apparatus of claim 10, wherein determining and learning the arrangement of the arbitrary electrodes comprises selecting, from a grid of the arbitrary electrodes, ones of the arbitrary electrodes depending on the variability of the biosignal obtained by the arbitrary electrodes, and the grid is physically arranged along the at least one direction and the second direction.

12. An operating method of a biosignal detection apparatus including a plurality of electrodes, the operating method comprising:

obtaining a biosignal through arbitrary electrodes of the plurality of electrodes of the biosignal detection apparatus;

determining, based on a number of the arbitrary electrodes along at least one direction of a sensor unit of the biosignal detection apparatus, a response time (RT) during which the arbitrary electrodes obtain the biosignal;

based on identifying a time within a period of the RT during which a waveform of the biosignal obtained by at least one of the arbitrary electrodes is determined to reach a stabilization, determining a variability of the biosignal obtained by the arbitrary electrodes; and based on the RT during which the arbitrary electrodes obtain the biosignal and the variability of the obtained biosignal satisfying a predetermined reference, determining an arrangement of the arbitrary electrodes and learning the determined arrangement of the arbitrary electrodes.

13. The operating method of claim 12, wherein the stabilization of the waveform is determined based on a preset signal-to-noise ratio.

14. The operating method of claim 12, wherein the determining and learning the arrangement of the arbitrary electrodes comprises controlling connection of at least one of a cathode, an anode, or a ground unit based on the predetermined reference.

15. The operating method of claim 12, wherein the determining and learning the arrangement of the arbitrary electrodes comprises learning an arrangement of modeled electrodes based on a preset first deep learning model and storing a learning result.

16. A computer-readable recording medium having recorded thereon a program for causing a computer to perform the operating method of claim 12.

17. A user terminal comprising:

a sensor unit comprising a plurality of electrodes configured to obtain a biosignal;

memory storing one or more instructions; and one or more processors configured to execute the one or more instructions to:

determine, based on identifying a number of arbitrary electrodes of the sensor unit, a response time (RT) during which the arbitrary electrodes of the plurality of electrodes obtain the biosignal, based on identifying a time within a period of the RT during which a waveform of the biosignal obtained by at least one of the arbitrary electrodes is determined to reach a stabilization, determine a variability of the biosignal obtained by the arbitrary electrodes, and based on the RT during which the arbitrary electrodes obtain the biosignal and the variability of the obtained biosignal satisfying a predetermined reference, determine and learn an arrangement of the arbitrary electrodes.

18. The user terminal of claim 17, wherein the one or more processors are further configured to execute the one or more instructions to learn the arrangement of the arbitrary electrodes by setting a function of the user terminal to be controlled based on gesture represented by the biosignal and the arrangement, and wherein the one or more processors are further configured
to execute the one or more instructions to:
receive a second biosignal from the sensor unit, and
control at least one of an operation of the user terminal
or haptic output of the sensor unit based on whether
the second biosignal is determined, based on the
learned arrangement and the function, to correspond
to the gesture.

19. The user terminal of claim 18, wherein the sensor unit is a band worn on a user, the biosignal and the second biosignal are from the user, and the arrangement is an arrangement of the any of the plurality of electrodes on a skin of the user.

* * * * *